United States Patent
Hu et al.

(10) Patent No.: US 6,730,417 B2
(45) Date of Patent: May 4, 2004

(54) ORGANIC ELECTROLUMINESCENT (EL) DEVICES

(75) Inventors: Nan-Xing Hu, Oakville (CA); Zoran D. Popovic, Mississauga (CA); Guerino G. Sacripante, Oakville (CA)

(73) Assignee: Xerox Corporation, Stamford, CT (US)

( * ) Notice: Subject to any disclaimer, the term of this patent is extended or adjusted under 35 U.S.C. 154(b) by 83 days.

(21) Appl. No.: 10/058,261

(22) Filed: Jan. 29, 2002

(65) Prior Publication Data

US 2003/0170490 A1 Sep. 11, 2003

(51) Int. Cl.$^7$ ............... H05B 33/12; C07D 251/14; C07D 49/00; C08G 61/12
(52) U.S. Cl. ............... 428/690; 428/917; 313/504; 313/506; 544/180; 526/261; 528/423
(58) Field of Search ............... 428/690, 917; 313/504, 506; 544/180; 526/261; 528/423

(56) References Cited

U.S. PATENT DOCUMENTS

| | | | |
|---|---|---|---|
| 3,530,325 A | | 9/1970 | Mehl et al. |
| 4,539,507 A | | 9/1985 | VanSlyke et al. |
| 4,720,432 A | | 1/1988 | VanSlyke et al. |
| 4,769,292 A | | 9/1988 | Tang et al. |
| 5,151,629 A | | 9/1992 | VanSlyke |
| 5,516,577 A | | 5/1996 | Matsuura et al. |
| 5,652,327 A | * | 7/1997 | Kang et al. ........... 528/327 |
| 5,728,801 A | | 3/1998 | Wu et al. |
| 5,962,631 A | | 10/1999 | Woo et al. |
| 6,057,048 A | | 5/2000 | Hu et al. |
| 6,225,467 B1 | | 5/2001 | Esteghamatian et al. |
| 6,229,012 B1 | | 5/2001 | Hu et al. |
| 6,352,791 B1 | * | 3/2002 | Fink et al. ........... 428/690 |
| 6,437,123 B1 | * | 8/2002 | Bock et al. ........... 544/216 |
| 2002/0132134 A1 | * | 9/2002 | Hu et al. ........... 428/690 |

FOREIGN PATENT DOCUMENTS

| | | | |
|---|---|---|---|
| WO | WO 90/13148 | | 11/1990 |
| WO | WO 98/11150 | * | 3/1998 |

OTHER PUBLICATIONS

Japanese Journal of Applied Physics, Part 2, vol. 34, L824 (1995).
G. Leising et al, Adv. Mater. 4 (1992) No. 1.
Friend et al, J. Chem. Soc., Chem. Commun. 1992, p. 32–34.
Norio Miyaura and Akira Suzuki, Chemical Review 1995, vol. 95, 2457.
A.B. Morgan et al, Journal of Applied Polymer Science 2000, vol. 76, 1257.
Friend et al, Physical Review B, vol. 42, No. 18, 11670.
Saito et al, Polymer, 1990, vol. 31, 1137.

* cited by examiner

*Primary Examiner*—Cynthia H. Kelly
*Assistant Examiner*—Dawn Garrett
(74) *Attorney, Agent, or Firm*—E. D. Palazzo

(57) ABSTRACT

A new class of conjugated organic polymers or copolymers comprising a triazine group. This class of polymers or copolymers may be used in organic electroluminescent (EL) devices.

17 Claims, No Drawings

ORGANIC ELECTROLUMINESCENT (EL) DEVICES

COPENDING APPLICATIONS

Illustrated in copending application U.S. Ser. No. 10/005, 930, filed Nov. 8, 2001, the disclosure of which is totally incorporated herein by reference, is an organic light emitting device comprising
(i) a first electrode;
(ii) a mixed region comprising a first hole transport material and a first electron transport material;
(iii) a second electrode;
(iv) an optional thermal protective layer coated on one of the first and second electrodes, wherein one of said first and second electrodes is a hole injection anode, and one of said electrodes is an electron injection cathode, and wherein the organic light emitting device further comprises at least one of
(v) a hole transport region interposed between said anode and said mixed region; and wherein said hole transport region is comprised of a second hole transport material, and which material is in contact with the mixed region; and
(vi) an electron transport region interposed between said cathode and said mixed region, and wherein said region is comprised of a second electron material, and which material is in contact with the mixed region; and containing at least one of
  a. said hole transport region (v) wherein said first hole transport material (ii) is similar to or dissimilar than said second hole transport material (v);
  b. said electron transport region (vi) wherein said first electron transport material (ii) is similar to or dissimilar than said second electron transport material; and wherein when a. is similar, b. is dissimilar; when a. is dissimilar, b. is similar or dissimilar; and when b. is dissimilar, a. is similar or dissimilar.

Illustrated in copending application U.S. Ser. No. 10/005, 404, filed Nov. 8, 2001, Publication No. 20030104242, the disclosure of which is totally incorporated herein by reference 1 is an organic light emitting device comprising:
(i) a first electrode;
(ii) a region comprising a mixture of (1) a tertiary aromatic amine, (2) a metal oxinoid, and (3) a red emitting material represented by

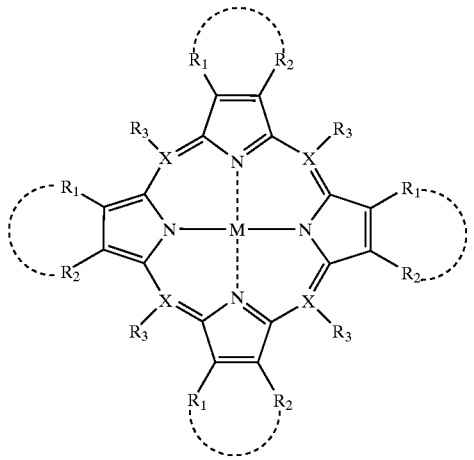

wherein X is a carbon C atom or a nitrogen N atom, or optionally oxygen or sulfur; $R_1$, $R_2$ and $R_3$ are each independently selected from the group consisting of hydrogen, alkyl, substituted alkyl, aryl, and substituted aryl; M is a divalent, trivalent or tetravalent metal;
(iii) a second electrode;
(iv) an optional protective element coated on at least one of the first and second electrodes; wherein one of said first and second electrodes is a hole injection anode, and one of said electrodes is an electron injection cathode; and at least one of
(v) a hole transport region situated between the anode and the region (ii), and wherein the hole transport region optionally includes a buffer layer; and
(vi) an electron transport region situated between the cathode and the region (ii), and wherein said red emitting component is present in an amount of from 1 to about 40 weight percent based on total weights of components in region (ii).

Illustrated in copending application U.S. Ser. No. 10/005, 518, tiled Nov. 8, 2001, Publication No. 20030104243, the disclosure of which is totally incorporated herein by reference, is an organic light emitting device comprising:
(i) a first electrode;
(ii) a mixed region comprising a mixture of (1) a tertiary aromatic amine, (2) a metal oxinoid, and (3) a green emitting coumarin dye of the Formula

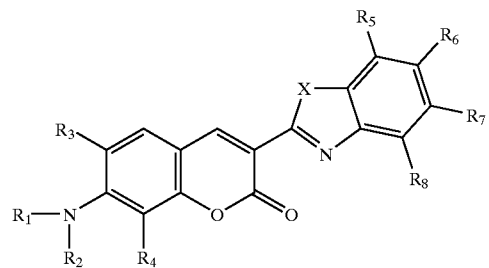

wherein X is selected from the group consisting of an oxygen atom, a sulfur atom, an alkyl imino group and aryl imino group; $R_1$ and $R_2$ are individually selected from the group consisting of alkyl, aryl, and carbocyclic; $R_3$ and $R_4$ are individually selected from the group consisting of a hydrogen atom, alkyl, and optionally a branched or unbranched 5 or 6 member substituent ring connecting with $R_1$ and $R_2$, respectively; and $R_5$, $R_6$, $R_7$, and $R_8$ are individually selected from the group consisting of a hydrogen atom, an alkoxy group and an alkyl group;
(iii) a second electrode;
(iv) an optional thermal protective element coated on one of the first and second electrodes; wherein one of the first and second electrodes is a hole injecting anode, and one of the first and second electrodes is an electron injecting cathode, and wherein the organic light emitting device further comprises at least one of
(v) a hole transport region interposed or situated between the anode and the mixed region, wherein the hole transport region optionally includes a buffer layer; and
(vi) an electron transport region interposed between the cathode and the mixed region, and wherein said green emitting dye is present in an amount of from about 0.01 to about 10 weight percent based on the total of said mixed layer components (ii).

Illustrated in copending application u.s. Ser. No. 10/005, 970, filed Nov. 8, 20013 Publication No. 20030104244, the disclosure of which is totally incorporated herein by reference, is an organic light emitting device comprising:

(i) an anode;

(ii) a hole transport layer comprising a mixture of a porphyrin and a hole transport material;

(iii) a mixed region comprising a mixture of (1) a hole transport material, and (2) an electron transport material, and which mixed region optionally contains an organic luminescent material;

(iv) a cathode; and wherein the organic light emitting device optionally further comprises at least one of (v) an electron transport region interposed between the mixed region and the cathode; and (vi) an optional thermal protective element coated on one of the anode and cathode.

Illustrated in copending application U.S. Ser. No. 10/005,993, filed Nov. 8, 2001, Publication No. 20030087125, the disclosure of which is totally incorporated herein by reference, is an organic light emitting device, comprising:

(i) a first electrode;

(ii) a region comprising a mixture of (1) N,N'-bis(p-biphenyl)-N,N'-diphenyl benzidine, and (2) an electron transport material, and which region further optionally comprises an organic luminescent material, and wherein said mixed region is capable of emitting light in response to hole-electron recombination;

(iii) a second electrode;

(iv) an optional thermal layer coated on at least one of the first and second electrodes, wherein one of said first and second electrodes is a hole injection anode, and one of said electrodes is an electron injection cathode, and wherein the organic light emitting device further comprises at least one of (v) a hole transport region interposed or situated between the first electrode and the mixed region; and (vi) an electron transport region interposed or situated between the mixed region and the cathode.

Illustrated in copending application U.S. Ser. No. 09/935,031, filed Aug. 22, 2001 on "OLEDs Having Light Absorbing Electrode," Publication No. 20030038593, the disclosure of which is totally incorporated herein by reference, is an organic light emitting device comprising:

a first electrode;

a second electrode; and a luminescent region including an organic electroluminescent material between the first electrode and the second electrode, wherein one of the first electrode and the second electrode includes both a substantially transparent charge injecting layer adjacent to the luminescent region and an electrically conductive light absorbing layer.

Illustrated in U.S. Pat. No. 6,392,339, filed on Jul. 20, 1999 on "Organic Light Emitting Devices Having Improved Efficiency and Operation Lifetime," the disclosure of which Is totally incorporated herein by reference, is an organic light emitting device, comprising, for example, a mixed region comprising a mixture of a hole transport material and an electron transport material, one of the hole transport material and the electron transport material being an emitter, the mixed region having a first surface and a second surface;

at least one of (i) a hole transport material on the first surface, and (ii) electron transport material on the second surface;

an anode in contact with the hole transport material on the first surface or with the first surface; and a cathode in contact with the electron transport material on the second surface or with the second surface; and U.S. Pat. No. 6,392,250, filed on Jun. 30, 2000 on "Organic Light Emitting Devices Having Improved Performance," the disclosure of which is totally incorporated herein by reference, is an organic light emitting device, comprising, for example, a mixed region having a first surface and a second surface, the mixed region comprising a mixture of a hole transport material, an electron transport material and at least one dopant, the dopant being an emitter, at least one of the hole transport material and the electron transport material optionally being an emitter;

at least one of (i) a hole transport region on the first surface, and (ii) an electron transport region on the second surface;

an anode in contact with the hole transport region on the first surface or with the first surface; and a cathode in contact with the electron transport region on the second surface or with the second surface.

Illustrated in copending application U.S. Ser. No. 09/800,716 (Now Abandoned), filed on Mar. 8, 2001 on "Cathodes for Electroluminescent Devices having Improved Contrast and Reduced Dark Spot Growth", the disclosure of which is totally incorporated herein by reference, is an electroluminescent device, comprising:

(i) a substrate;

(ii) a first electrode;

(iii) a mixed region comprising a mixture of a hole transport material and an electron transport material, and wherein this mixed region includes at least one organic luminescent material;

(iv) a second electrode;

(v) a thermal protective element coated on the second electrode, wherein one of the two said first and second electrodes is a hole injection anode, and one of the two said electrodes is an electron injection cathode, and wherein the organic light emitting device further comprises;

(vi) a hole transport region, interposed between the anode and the mixed region, wherein the hole transport region optionally includes a buffer layer; and (vii) an electron transport region interposed between the second electrode and the mixed region.

Illustrated in copending application U.S. Ser. No. 09/770,154, filed on Jan. 26, 2001 on "Electronluminescent Devices," Publication No. 20020145380, the disclosure of which is totally incorporated herein by reference, is disclosed an organic light emitting device comprising in sequence a substrate;

a first electrode;

a light emitting region comprising an organic luminescent material; and a second electrode, and a thermal protective element.

Illustrated in copending application U.S. Ser. No. 09/800,716, filed on Mar. 8, 2001 on "Cathodes for Electroluminescent Devices having Improved Contrast and Reduced Dark Spot Growth", the disclosure of which is totally incorporated herein by reference, is an electroluminescent device, comprising:

a first electrode;

a second electrode; and a luminescent region between the first electrode and the second electrode, wherein one of the first electrode and the second electrode comprises a metal-organic mixed region including:

a metal;

an organic material; and at least one component selected from the group consisting of metals, organic materials and inorganic materials.

FIELD OF THE INVENTION

The present invention relates generally to a new class of conjugated organic polymers or copolymers, which may be used in organic electroluminescent (EL) devices to improve performance characteristics, such as uniform luminescence, electroluminescent efficiency, durability, and driving voltages. These organic electroluminescent (EL) devices may be selected for use in flat-panel emissive display technologies, including TV screens, computer screens, and the like.

BACKGROUND OF THE INVENTION

A simple organic EL device can be comprised of a layer of an organic luminescent material conductively sandwiched between an anode, typically comprised of a transparent conductor such as indium tin oxide, and a cathode, typically a low work function metal such as magnesium, calcium, aluminum, or the alloys thereof with other metals. The EL device functions on the principle that under an electric field, positive charges (holes) and negative charges (electrons) are respectively injected from the anode and cathode into the luminescent layer and undergo recombination to form excitonic states which subsequently emit light. A number of prior art organic EL devices have been prepared from a laminate of an organic luminescent material and electrodes of opposite polarity. Some devices include a single crystal material, such as single crystal anthracene, as the luminescent substance as described in U.S. Pat. No. 3,530,325. These devices, however, require excitation voltages on the order of 100 electron volts or greater.

An organic EL device with a multilayer structure can be formed as a dual layer structure comprising one organic layer adjacent to the anode, which supports hole transport, and another organic layer adjacent to the cathode, which supports electron transport and acts as the organic luminescent zone of the device. Another alternate device configuration is comprised of three separate layers, a hole transport layer, a luminescent layer, and an electron transport layer, which layers are laminated in sequence and are sandwiched between an anode and a cathode, respectively. Optionally, a fluorescent dopant material can be added to the emission zone or layer whereby the recombination of charges results in the excitation of the fluorescent dopant material.

In U.S. Pat. No. 4,539,507 there is disclosed an EL device formed of a conductive glass transparent anode, a hole transporting layer of 1,1-bis(4-p-tolylaminophenyl) cyclohexane, an electron transporting layer of 4,4'-bis(5,7-di-tert-pentyl-2-benzoxzolyl)stilbene, and an indium cathode.

U.S. Pat. No. 4,720,432 discloses an organic EL device comprising a dual-layer hole injecting and transporting zone, one layer being comprised of porphyrinic compounds supporting hole injection and the other layer being comprised of aromatic tertiary amine compounds supporting hole transport.

U.S. Pat. No. 4,769,292 discloses an EL device employing a luminescent zone comprised of an organic host material capable of sustaining hole-electron recombination and a fluorescent dye material capable of emitting light in response to energy released by hole-electron recombination. A preferred host material is an aluminum complex of 8-hydroxyquinoline, namely tris(8-hydroxyquinolinate) aluminum.

Typically, organic EL devices with multi-layered configurations comprise an electron transport layer in contact with a cathode. This electron transport layer is intended to assist injection of electrons from the cathode into the light-emitting layer. A variety of organic electron transport materials have been employed for this purpose. A class of such electron transport materials is comprised of the metal complexes of 8-hydroxyquinoline, as disclosed in U.S. Pat. No. 4,720,432 and herein incorporated by reference. Other classes of electron transport materials for EL devices are 1,3,5-oxidiazole derivatives, such as those disclosed in the Japanese Journal of Applied Physics, Part 2, vol. 34, L824 (1995), and 1,3,5-triazine derivatives, as disclosed in U.S. Pats. Nos. 6,057,048, 6,225,467 and 6,229,012; herein incorporated by reference.

While recent progress in organic EL research has elevated the potential of organic EL devices for widespread applications, the performance levels of current available devices may still be below expectations. Further, for visual display applications, organic luminescent materials should provide a satisfactory color in the visible spectrum, normally with emission maxima at about 460, 550 and 630 nanometers for blue, green and red. In most conventional organic EL devices, the luminescent zone or layer is formed of a green-emitting luminophor of tris(8-hydroxyquinolinate) aluminum with certain fluorescent materials. Although this material may be suitable for use in EL devices with light emission in green or longer wavelength regions, for blue-emitting EL devices they are of limited use. While there has been several disclosures describing blue-emitting organic EL devices, for example, in U.S. Pat. Nos. 5,151,629 and 5,516,577, their performance characteristics still possess many disadvantages such as poor emission hue, high operation voltages, low luminescence, and poor operation stability. Thus, there continues to be a need for improved luminescent compositions for organic EL devices.

Typically, the production of organic EL devices, using the afore-mentioned low-molecular weight organic compounds, is achieved by vapour-deposition. These EL devices have a high production cost and the vapour-deposited amorphous layer is prone to morphological changes which can cause a reduction in the intensity of electroluminescence and the operating time.

In contrast, polymeric substances for use in the production of organic EL devices are characterized by good mechanical and thermal stability. In addition, the production of large surface area light-emitting elements can be enabled due to the possibility of casting and spin-coating polymeric substances.

Polymeric organic luminescent compositions used in organic EL devices are polymers such as poly-(p-phenylenes), polyfluorenes and poly-(p-phenylvinylenes): G. Leising et al., Adv. Mater. 4 (1992) No. 1; Friend et al., J. Chem. Soc., Chem. Commun. 1992, p. 32–34; Saito et al., Polymer, 1990, Vol. 31, 1137; Friend et al., Physical Review B, Vol. 42, No. 18, 11670, International Patent Application No. WO 90/13148 and U.S. Pat. No. 5,962,631, herein incorporated by reference. The use of these particular polymers in organic EL devices, however, requires a highly active cathode, such as calcium. This highly active cathode is required to provide enough energy for electron injection into these types of polymers in order to induce luminescence. For organic EL devices comprising these types of polymers, poor electron injection in organic EL devices remains a concern. Copolymers of these conjugated polymers with certain chromophors having high electron affinity, such as 1,3,4-oxidiazoles, have been developed to improve electron transport properties. The intrinsic instability of these chromophors, however, generally results in poor device stability.

There is a need for polymeric organic compositions that have improved electron transport properties, as well as improved electron injection properties. These polymeric organic compositions may be utilized as either a luminescent/electron transport material, or simply an electron transport material, that will provide both desirable electronic properties and good device stability, for instance, enhance the charge transporting characteristics of organic EL devices, thus lowering device driving voltages.

There is also a need for polymeric organic compositions which are capable of providing uniform and satisfactory emission in the visible spectrum from blue to red colors, in particular, efficient blue luminescent materials for organic EL devices.

SUMMARY OF THE INVENTION

It is a feature of the present invention to provide improved EL devices. More specifically, a feature of the present invention relates to a polymeric organic composition that has improved electron transport properties, as well as improved electron injection properties and may be utilized as either a luminescent/electron transport material, or simply an electron transport material, that will provide both desirable electronic properties and good device stability.

It is another feature of the present invention to provide a polymer that is capable of enhancing the charge transporting characteristics of EL devices, thus lowering device driving voltages.

It is still a further feature of the present invention to provide a polymeric composition which is capable of providing uniform and satisfactory emission in the visible spectrum from blue to red colors, in particular, efficient blue emission.

It is yet another feature of the present invention to provide an n (negative)-type semiconductor (a semiconductor enriched with electrons and having small band gaps), in particular, an n (negative)-type conjugated polymer.

It is another feature of the present invention to provide new luminescent materials comprised of fluorescent triazine copolymers, which unlike certain EL devices that utilize an oxidiazole copolymer, may provide good device stability.

In embodiments, there is provided a triazine compound selected from the group consisting of:

a triazine compound of Formula I:

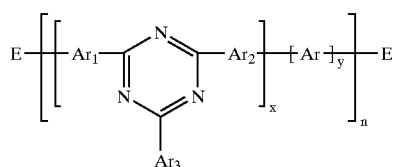

(I)

a triazine compound of Formula II:

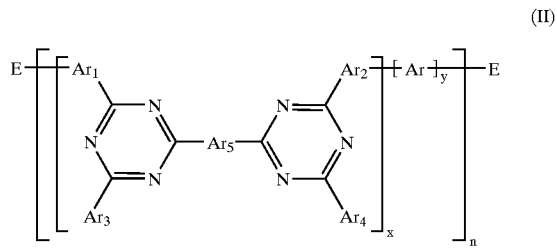

(II)

a triazine compound of Formula III:

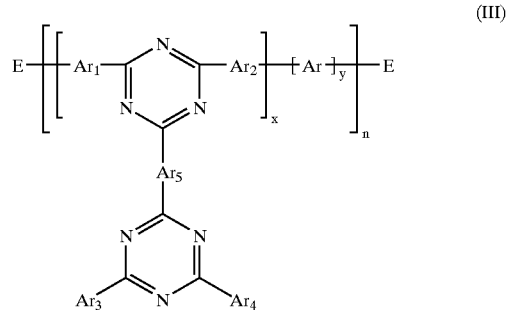

(III)

wherein E is an end-capping group; Ar, $Ar_1$, $Ar_2$, $Ar_3$, $Ar_4$ and $Ar_5$ are each independently selected from the group consisting of an aromatic group and a heteroaromatic group containing nitrogen, oxygen or sulfur; x and y each represent molar fractions of the corresponding monomers, wherein the total molar fraction of x and y is 1; and n represents a number of repeating units.

In embodiments, the compounds of Formulas I, II and III each independently represent at least one of an alternating copolymer, a random copolymer, a block copolymer and a graft copolymer.

Typically, at least one of the aromatic group and the heteroaromatic group each independently contain from about 6 to 20 carbons and/or at least one of the aromatic group and the heteroaromatic group contains from about 6 to 20 carbons and at least one substituent selected from the group consisting of a halide; an alkyl group containing from about 1 to 20 carbons; an alkoxy group containing from about 1 to about 20 carbons; a phenoxy group; and a cyano group.

In embodiments, there is provided a triazine compound selected from the group consisting of Formulas I, II and III, wherein the Ar, $Ar_1$, $Ar_2$, and $Ar_5$ are each independently selected from the group consisting of:

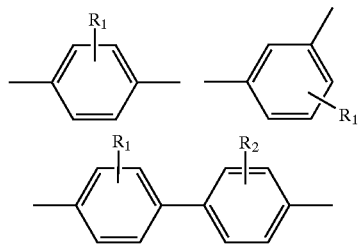

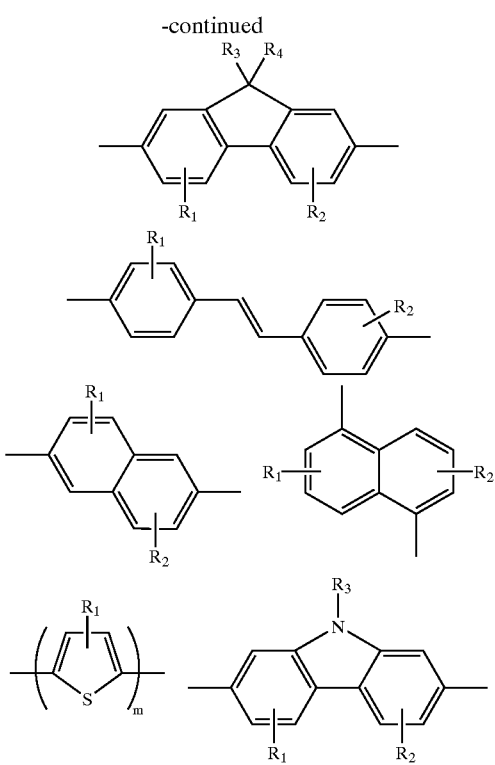

wherein $R_1$ and $R_2$ are each independently selected from the group consisting of a hydrogen, a halide, an alkyl group containing from about 1 to 20 carbons, an aromatic group, a heteroaromatic group containing nitrogen, oxygen or sulfur, an alkoxy group containing from about 1 to 20 carbons, a phenoxy group, and a cyano group; $R_3$ and $R_4$ are each independently selected from the group consisting of a hydrogen; a fluorine, an alkyl group containing from about 1 to 20 carbons; an alkyl group containing from about 1 to 20 carbons and at least one heteroatom selected from the group consisting of oxygen, sulfur, and silicon; an aromatic group; a heteroaromatic group containing nitrogen, oxygen or sulfur; an alkoxy group containing from about 1 to 20 carbons; a phenoxy group; a cyano group; and m is an integer from 1 to about 6.

Typically, at least one of the aromatic group and the heteroaromatic group each independently contain from about 6 to 20 carbons and/or at least one of the aromatic group and the heteroaromatic group each independently contain from about 6 to 20 carbons and at least one substituent selected from the group consisting of a halide; an alkyl group containing from about 1 to 20 carbons; an alkoxy group containing from about 1 to about 20 carbons; a phenoxy group; and a cyano group.

Typically, at least one of the $Ar_3$ and the $Ar_4$ are selected from the group consisting of a phenyl group, a biphenyl group, a naphthyl group, a stilbenyl group, a fluorenyl group and substituted groups thereof, wherein the substituted groups contain at least one substituent selected from the group consisting of a halide, an alkyl group containing from about 1 to 20 carbons; an alkoxy group containing from about 1 to about 20 carbons; a phenoxy group; and a cyano group.

In embodiments, x is about 0.01 to 1, y is less than about 0.99, and n is a number of from about 3 to about 500. Preferably, x is about 0.05 and y is about 0.95.

Preferably, E is selected from the group consisting of a hydrogen, a halide, an alkyl group, an alkoxy group and an aryl group.

Preferably, the Mw (weight average molecular weight) of the triazine compound is from about 1,000 to 100,000.

In embodiments, there is provided a triazine compound selected from the group consisting of:
a triazine compound of Formula IV:

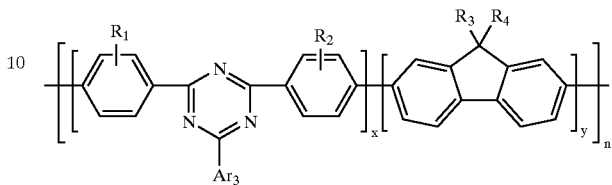

a triazine compound of Formula V:

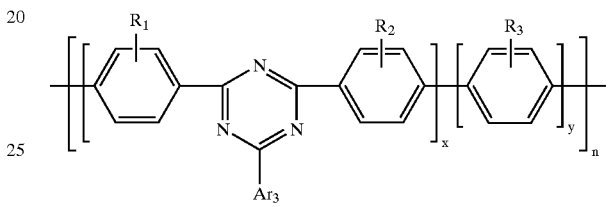

a triazine compound of Formula VI:

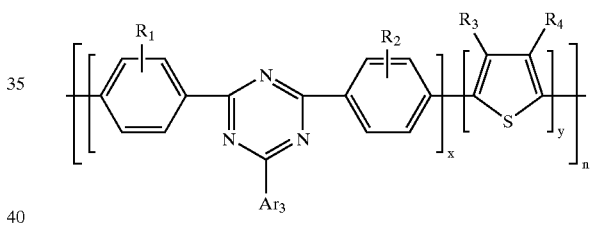

wherein $R_1$ and $R_2$ are each independently selected from the group consisting of a hydrogen, a halide, an alkyl group containing from about 1 to 20 carbons, an aromatic group, a heteroaromatic group containing nitrogen, oxygen or sulfur, an alkoxy group containing from about 1 to 20 carbons, a phenoxy group, and a cyano group; $R_3$ and $R_4$ are each independently selected from the group consisting of a hydrogen; a fluorine; an alkyl group containing from about 1 to 20 carbons; an alkyl group containing from about 1 to 20 carbons and at least one heteroatom selected from the group consisting of oxygen, sulfur, and silicon; an aromatic group; a heteroaromatic group containing nitrogen, oxygen or sulfur; an alkoxy group containing from about 1 to 20 carbons; a phenoxy group; a cyano group; and Ar3 is selected from the group consisting of an aromatic group and a heteroaromatic group containing nitrogen, oxygen or sulfur; x and y each represent molar fractions of the corresponding monomers, wherein the total molar fraction of x and y is 1; and n represents a number of repeating units.

In embodiments, the compounds of Formulas IV, V and VI each independently represent at least one of an alternating copolymer, a random copolymer, a block copolymer and a graft copolymer.

Typically, at least one of the aromatic group and the heteroaromatic group each independently contain from about 6 to 20 carbons and/or at least one of the aromatic group and the heteroaromatic group contains from about 6 to 20 carbons and at least one substituent selected from the group consisting of a halide; an alkyl group containing from about 1 to 20 carbons; an alkoxy group containing from about 1 to about 20 carbons; a phenoxy group; and a cyano group.

In embodiments, x is about 0.01 to 1, y is less than about 0.99, and n is a number of from about 3 to about 500. Preferably, x is about 0.05 and y is about 0.95.

In embodiments, there is provided an electroluminescent device comprising an anode, a cathode, and an organic film/layer between the anode and cathode, wherein the organic film/layer is comprised of a triazine compound selected from the group consisting of Formulas I to VI.

In embodiments, there is provided an electroluminescent device comprising, in sequence, an anode, a hole transport layer, an electron transport layer and a cathode, wherein the electron transport layer is comprised of a triazine compound selected from the group consisting of Formulas I to VI. Preferably, the hole transport layer is selected from a group consisting of polyaniline and its acid-doped forms, polythiophene and its acid-doped forms, polycarbazoles, and polymeric arylamines.

In embodiments, there is provided an electroluminescent device comprising, in sequence, an anode, a hole transport layer, a light emitting layer, an electron transport layer and a cathode, wherein the light emitting layer or the electron transport layer is comprised of a triazine compound selected from the group consisting of Formulas I to VI. Preferably, the light emitting layer is an organic polymer selected from the group consisting of poly-(p-phenylenes), polyfluorenes and poly-(p-phenylvinylenes).

In embodiments, there is provided an electroluminescent device comprising, in sequence, an anode, a hole transport layer, an electron transport layer and a cathode, wherein the electron transport layer is comprised of a triazine compound of Formula IV. Preferably, Ar3 is selected from the group consisting of a phenyl, a biphenyl and a stilbenyl group; R1 and R2 are each hydrogen; R3 and R4 are each independently an alkyl group containing from about 5 to 20 carbons.

In embodiments, the hole transport layer is selected from a group consisting of polyaniline and its acid-doped forms, polythiophene and its acid-doped forms, polycarbazoles, and polymeric arylamines.

DESCRIPTION OF EMBODIMENTS

In embodiments, there is provided a new class of conjugated polymers or copolymers comprising a triazine group. More specifically, the triazine polymers or copolymers of the present invention, which may be selected as luminescent/electron transport compositions for organic EL devices, may be comprised of the triazine copolymers illustrated in Formulas I, II, and III:

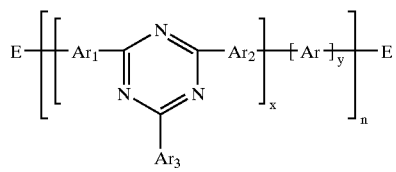
(I)

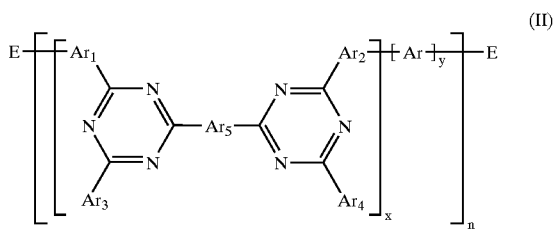
(II)

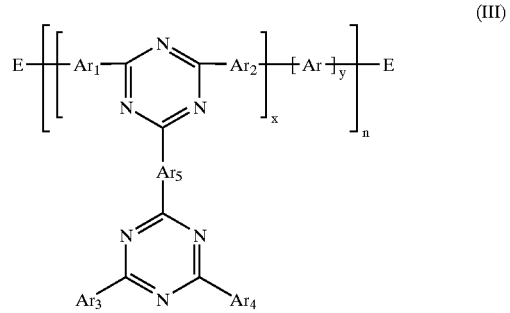
(III)

wherein E is an end-capping group. Preferably, E is selected from the group consisting of a hydrogen, a halide, an alkyl group, an alkoxy group and an aryl group. The aryl group may be either substituted or unsubstituted. Preferably, the unsubstituted aryl group contains from about 6 to 20 carbons and the substituted aryl group contains from about 6 to 20 carbons and at least one substituent selected from the group consisting of an alkyl group containing from about 1 to 20 carbons, an alkoxy group, a trialkoxysiloxy group, and the like. With respect to the triazine copolymers, Formulas I, II and III represent alternating copolymers, random copolymers, block copolymers and/or graft copolymers Ar, $Ar_1$, $Ar_2$, and $Ar_5$ may each be independently selected from the group consisting of an aromatic group and a heteroaromatic group containing nitrogen, oxygen or sulfur. These aromatic and heteroaromatic groups may be either substituted or unsubstituted. Preferably, the unsubstituted aromatic and heteroaromatic groups each contain from about 6 to 20 carbons and the substituted aromatic and heteroaromatic groups each independently contain from about 6 to 20 carbons and at least one substituent selected from the group consisting of a halide (for organic EL devices, it is preferably fluorine), an alkyl group containing from about 1 to 20 carbons, an alkoxy group containing from about 1 to about 20 carbons, a phenoxy group, a cyano group, and the like. Some examples of Ar, $Ar_1$, $Ar_2$, and $Ar_5$ disclosed herein are listed below:

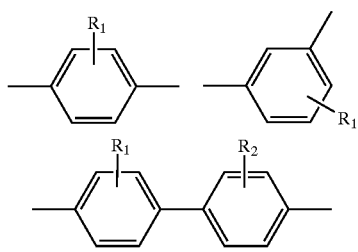

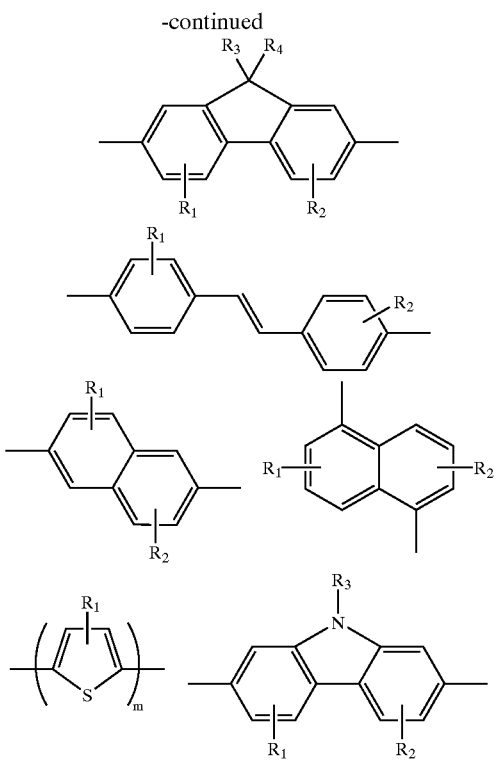

wherein $R_1$ and $R_2$ may each be independently selected from the group consisting of a hydrogen, a halide (for organic EL devices, it is preferably fluorine), an alkyl group containing from about 1 to 20 carbons, an aromatic group, a heteroaromatic group containing nitrogen, oxygen or sulfur, an alkoxy group containing from about 1 to 20 carbons, a phenoxy group, a cyano group, and the like. The aromatic and heteroaromatic groups may be either substituted or unsubstituted. Preferably, the unsubstituted aromatic and heteroaromatic groups each independently contain from about 6 to 20 carbons and the substituted aromatic and heteroaromatic groups each independently contain from about 6 to 20 carbons and at least one substituent selected from the group consisting of a halide (for organic EL devices, it is preferably fluorine), an alkyl group containing from about 1 to 20 carbons, an alkoxy group containing from about 1 to about 20 carbons, a phenoxy group, a cyano group, and the like.

$R_3$ and $R_4$ may each be independently selected from the group consisting of a hydrogen; a fluorine; an alkyl group containing from about 1 to 20 carbons; an alkyl group containing from about 1 to 20 carbons and at least one heteroatom selected from the group consisting of oxygen, sulfur, and silicon; an alkoxy group containing from about 1 to 20 carbons; a phenoxy group; a cyano group; an aromatic group; a heteroaromatic group containing nitrogen, oxygen or sulfur; and the like. The aromatic and heteroaromatic groups may be either substituted or unsubstituted. Preferably, the unsubstituted aromatic and heteroaromatic groups each independently contain from about 6 to 20 carbons and the substituted aromatic and heteroaromatic groups each independently contain from about 6 to 20 carbons and at least one substituent selected from the group consisting of a halide (for organic EL devices, it is preferably fluorine), an alkyl group containing from about 1 to 20 carbons, an alkoxy group containing from about 1 to about 20 carbons, a phenoxy group, a cyano group, and the like. Also, both $R_3$ and $R_4$ at carbon-9 of the fluorene group may form a combined ring structure containing from about 5 to 20 atoms. M is an integer from 1 to about 6.

$Ar_3$ and $Ar_4$ may each be independently selected from the group consisting of an aromatic group and a heteroaromatic group containing nitrogen, oxygen or sulfur. These aromatic and heteroaromatic groups may be either substituted or unsubstituted. Preferably, the unsubstituted aromatic and heteroaromatic groups each independently contain from about 6 to 20 carbons and the substituted aromatic and heteroaromatic groups each independently contain from about 6 to 20 carbons and at least one substituent selected from the group consisting of a halide (for organic EL devices, it is preferably fluorine), an alkyl group containing from about 1 to 20 carbons, an alkoxy group containing from about 1 to about 20 carbons, a phenoxy group, a cyano group, and the like. Some preferred examples of $Ar_3$ and $Ar_4$ include a phenyl, a biphenyl, a naphthyl, a stilbenyl, and a fluorenyl group, which all may further contain a substituent selected from the group consisting of a halide (for organic EL devices, it is preferably fluorine), an alkyl group containing from about 1 to 20 carbons, an alkoxy group containing from about 1 to about 20 carbons, a phenoxy group, a cyano group, and the like.

In formulas I, II, and III, x and y each represent the molar fractions of the corresponding monomers, wherein the total molar fraction of x and y is 1. X may be from about 0.01 to 1, while y may be less than about 0.99. Preferably, x is about 0.05 and y is about 0.95. N represents a number of repeating units. Preferably, n is from about 3 to about 500; n is more preferably 10 to about 200. Preferably, the Mw (weight average molecular weight) of the triazine polymer or copolymer is from about 1,000 to 100,000.

Preferred embodiments of the conjugated polymers or copolymers of the present invention are represented by the following formulas IV, V, and VI:

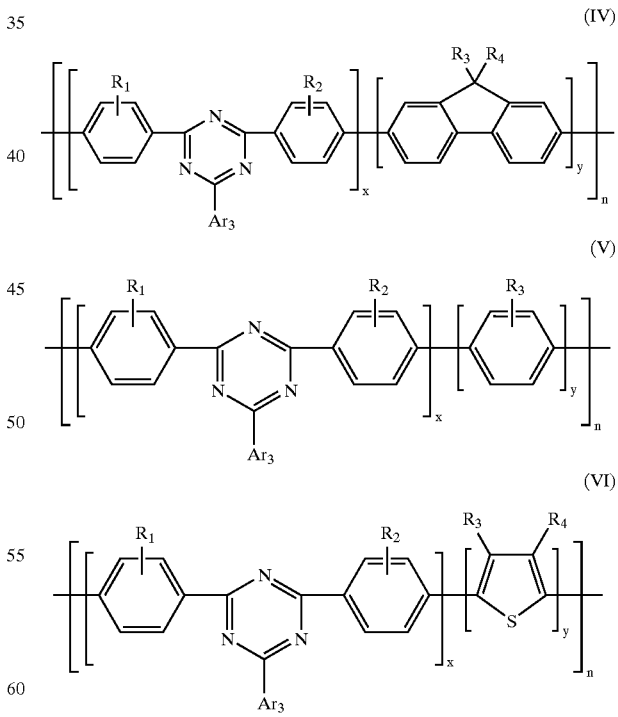

wherein $R_1$ and $R_2$ may each independently represent a hydrogen, a halide (for organic EL devices it is preferably, fluorine), an alkyl group containing from about 1 to 20 carbons, an aromatic group, a heteroaromatic group containing nitrogen, oxygen or sulfur, an alkoxy group containing from about 1 to 20 carbons, a phenoxy group, a cyano group, and the like. The aromatic and heteroaromatic groups may be either substituted or unsubstituted. Preferably, the unsubstituted aromatic and heteroaromatic groups each independently contain from about 6 to 20 carbons and the substituted aromatic and heteroaromatic groups each independently contain from about 6 to 20 carbons and at least one substituent selected from the group consisting of a halide (for organic EL devices, it is preferably fluorine), an alkyl group containing from about 1 to 20 carbons, an alkoxy group containing from about 1 to about 20 carbons, a phenoxy group, a cyano group, and the like.

$R_3$ and $R_4$ may each independently represent a hydrogen; a fluorine; an alkyl group containing from about 1 to 20 carbons; an alkyl group containing from about 1 to 20 carbons and at least one heteroatom selected from the group consisting of oxygen, sulfur, and silicon; an alkoxy group containing from about 1 to 20 carbons; a phenoxy group; a cyano group; an aromatic group; a heteroaromatic group containing nitrogen, oxygen or sulfur; and the like. The aromatic and heteroaromatic groups may be either substituted or unsubstituted. Preferably, the unsubstituted aromatic and heteroaromatic groups each independently contain from about 6 to 20 carbons and the substituted aromatic and heteroaromatic groups each independently contain from about 6 to 20 carbons and at least one substituent selected from the group consisting of a halide (for organic EL devices, it is preferably fluorine), an alkyl group containing from about 1 to 20 carbons, an alkoxy group containing from about 1 to about 20 carbons, a phenoxy group, a cyano group, and the like. Specifically, both $R_3$ and $R_4$ at carbon-9 of the fluorene group may form a combined ring structure containing from about 5 to 20 atoms. $Ar_3$ may be selected from the group consisting of an aromatic group and a heteroaromatic group containing nitrogen, oxygen or sulfur. These aromatic and heteroaromatic groups may be either substituted or unsubstituted. Preferably, the unsubstituted aromatic and heteroaromatic groups each independently contain from about 6 to 20 carbons and the substituted aromatic and heteroaromatic groups each independently contain from about 6 to 20 carbons and at least one substituent selected from the group consisting of a halide (for organic EL devices, it is preferably fluorine), an alkyl group containing from about 1 to 20 carbons, an alkoxy group containing from about 1 to about 20 carbons, a phenoxy group, a cyano group, and the like. Some preferred examples of $Ar_3$ include a phenyl, a biphenyl, a naphthyl, a stilbenyl, and a fluorenyl group, which all may further contain a substituent selected from the group consisting of a halide (for organic EL devices, it is preferably fluorine), an alkyl group containing from about 1 to 20 carbons, an alkoxy group containing from about 1 to about 20 carbons, a phenoxy group, a cyano group, and the like.

The conjugated polymeric or copolymeric triazine compositions of the present invention may be prepared by standard synthetic processes. Specifically, the copolymers may be synthesized using a palladium-catalyzed coupling reaction referred to as the Suzuki reaction, which is described in Norio Miyaura and Akira Suzuki, Chemical Review 1995, Vol. 95, 2457, herein incorporated by reference. In an illustrative example, the triazine copolymer of Formula IV, may be synthesized as illustrated in Scheme I:

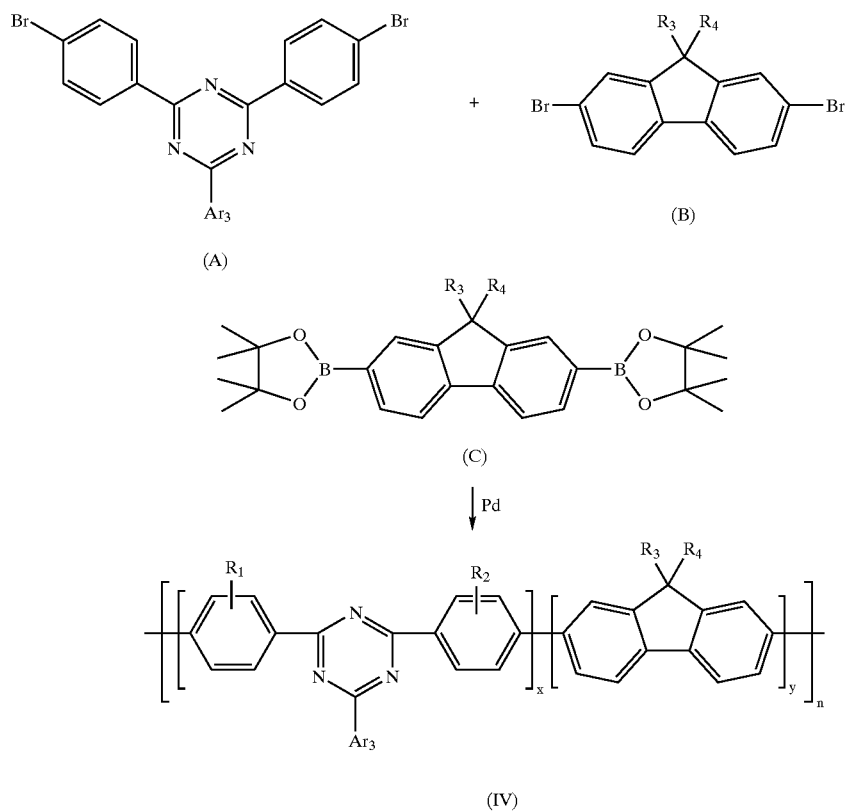

The monomer precursors may be prepared according to literature procedures. For instance, the triazine monomer precursor (A) can be prepared using a similar procedure as that described in U.S. Pat. No. 6,225,467, herein incorporated by reference. The monomer precursor (B) may be prepared using a similar procedure as that described in U.S. Pat. No. 5,962,631, herein incorporated by reference. The monomer precursor (C) may be prepared from monomer precursor (B) using a similar procedure as that described in A. B. Morgan et al., Journal of Applied Polymer Science 2000, Vol. 76, 1257, herein incorporated by reference.

The polymerization itself is conducted using a two-phase system (for example, an aqueous-toluene system) with the aid of a phase-transfer agent and a palladium catalyst. Specifically, a triazine copolymer containing a molar fraction 'x' of a triazine structural unit and a molar fraction 'y' of an Ar structural unit, such as a fluorene unit, may be prepared as follows: in a suitable glass reactor, there is added x mole fraction of monomer (A), such as 2,6-bis(4-bromophenyl)-4-phenyl-1,3,5-triazine, 0.5 y mole fraction of monomer (B), such as 9-di-n-octyl-2,7-dibromofluorene, and 0.5 y mole fraction of monomer (C), such as 9,9-di-n-octyl-2,7-bis(4,4,5,5-tetramethyl-1,3,2-dioxaborolan-2-yl)fluorene. The mixture is dissolved in a suitable organic solvent, such as toluene, benzene, or xylene. Into the resulting organic mixture there is added an aqueous inorganic base solution in a concentration of from 0.5 M to about 3 M. Suitable inorganic bases include sodium carbonate, potassium carbonate, sodium hydroxide and the like. Preferably a phase transfer catalyst, such as Aliquat-336™ (commercially available from Aldrich Chemicals, Milwaukee, Wis., USA), is added. The reaction is, preferably, conducted under oxygen-free conditions, for example, under an argon or nitrogen atmosphere. After the reaction mixture is saturated with argon or nitrogen, about 1 to 10 mol % (based on monomer C) of a suitable palladium catalyst is added. Useful examples of a suitable palladium catalyst include palladium acetate, tetrakis-(triphenylphosphine) palladium, tetrakis-(triphenylphosphine) palladium chloride and the like. The polymerization is carried out at a temperature from about 30° C. to about 200° C., preferably from about 60° C. to about 150° C. and preferably for about 15 hours. After cooling the reaction mixture to room temperature, approximately 23° C., the organic phase containing the polymer products is separated from the aqueous phase. The polymer products may be precipitated from a suitable solvent, such as methanol, ethanol, acetone and the like. The triazine polymers or copolymers obtained may be confirmed by elemental analysis, NMR or IR spectrometric identification techniques.

Specific examples of triazine copolymers of Formulas IV to VI include the following copolymers of Formulas VII to XIV:

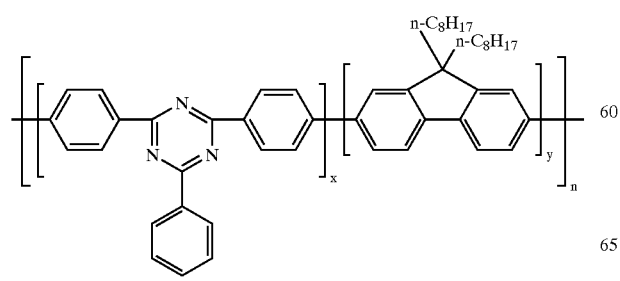
(VII)

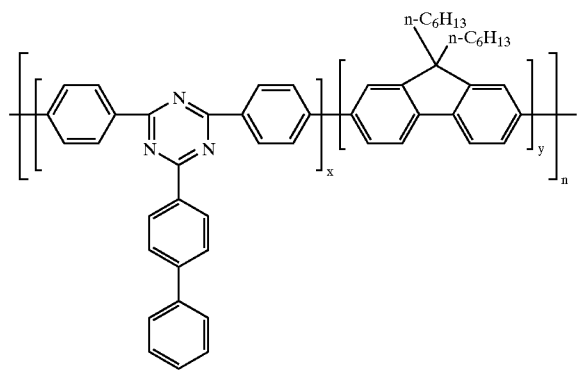
(VIII)

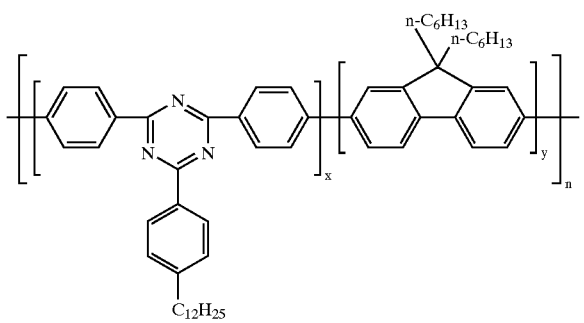
(IX)

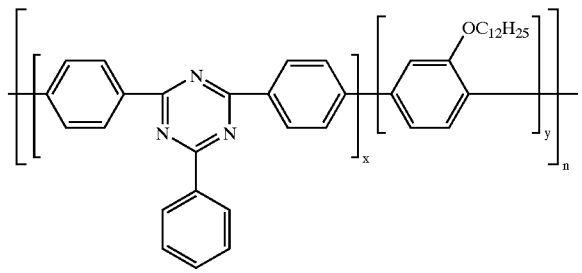
(X)

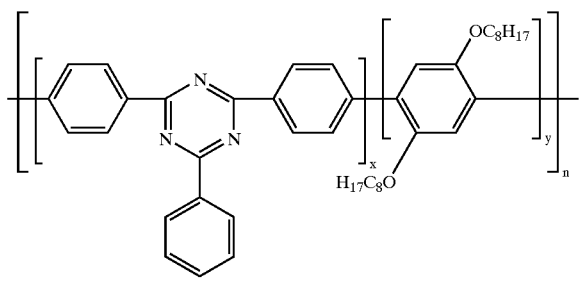
(XI)

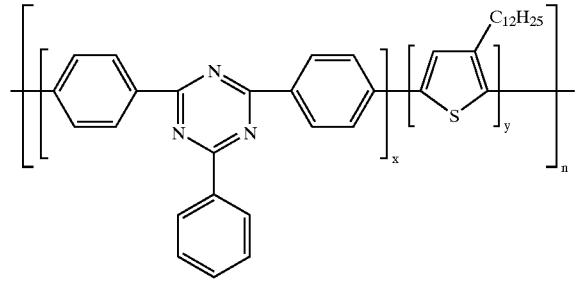
(XII)

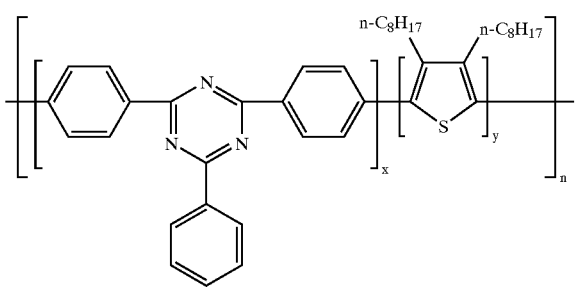

(XIII)

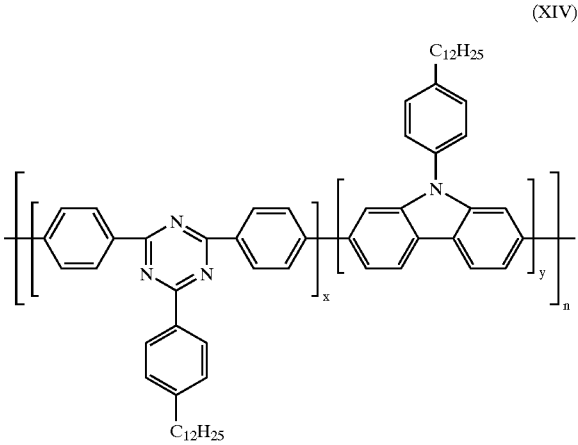

(XIV)

In embodiments of the present invention, the triazine polymers or copolymers of the present invention may be used to form thin films/layers. Such films/layers may be used as a light emitting layer or a charge transport layer in organic electroluminescent devices. These films may be prepared using various means well known in the art, including spin-coating, spray-coating, dip-coating, roller-coating, screen-coating and the like.

In an embodiment of the present invention, an organic EL device may comprise an anode, a cathode, and an organic film/layer between the anode and cathode. The organic film/layer comprised of a triazine polymer or copolymer disclosed herein. In another embodiment of the present invention, an organic EL device may comprise, in sequence, an anode, a hole transport layer, an electron transport layer and a cathode. The electron transport layer comprised of a triazine polymer or copolymer disclosed herein. In yet another embodiment, an organic EL device may comprise, in sequence, an anode, a hole transport layer, a light emitting layer, an electron transport layer and a cathode. The light emitting layer or the electron transport layer may be comprised of a triazine polymer or copolymer disclosed herein.

In a preferred embodiment, an organic EL device is provided wherein light emission originates from an organic film/layer. The organic EL device comprises, in sequence, an anode such as indium tin oxide coated on a glass substrate, the organic film/layer comprised of a triazine polymer or copolymer disclosed herein, and a cathode, such as a low work function metal, for example, magnesium.

In another preferred embodiment, an organic EL device is provided wherein light emission originates from a hole transport layer and/or an electron transport layer. The organic EL device comprises, in sequence, an anode, the hole transport layer, the electron transport layer and a cathode. The anode is, for example, indium tin oxide coated on a glass substrate. In contact with the anode is the hole transport layer comprised of, for example, a material comprising a tertiary aromatic amine group. The electron transport layer comprises a triazine polymer or copolymer disclosed herein and the cathode is, for example, a low work function metal such as magnesium.

In another preferred embodiment, an organic EL device is provided wherein light emission originates from a hole transport layer and/or an organic film/layer. The organic EL device comprises, in sequence, an anode, the hole transport layer, the organic film/layer, an electron transport layer and a cathode. The anode is, for example, indium tin oxide coated on a glass substrate. In contact with the anode is the hole transport layer comprised of, for example, a material comprising a tertiary aromatic amine group. The organic film/layer comprises a triazine polymer or copolymer disclosed herein. The electron transport layer comprises, for example, a metal chelate of 8-hydroxyquinoline and the cathode is, for example, a low work function metal such as magnesium.

In yet another preferred embodiment of the invention, an organic EL device is provided wherein light emission originates from a light emitting layer. The organic EL device comprises, in sequence, an anode, a hole transport layer, the light emitting layer, a electron transport layer and a cathode. The anode is, for example, indium tin oxide coated on a glass substrate. In contact with the anode is the hole transport layer comprised of, for example, a material comprising a tertiary aromatic amine group. The light emitting layer comprises a polymeric luminescent material, for example, a polyfluorene material. The electron transport layer comprises a triazine polymer or copolymer disclosed herein. The cathode is, for example, a low work function metal such as magnesium.

The preferred thicknesses of the layers of the present invention are as follows:

The support substrate (eg. glass substrate) is preferably of from about 25 to about 5,000 microns or more, and, more preferably, of from about 500 to about 2000 microns, depending, for example, on the structural demands of the device. Typically, glass substrate, having a thickness of 1000 microns, is used.

The anode layer is preferably of from about 1 to about 500 nanometers and more preferably, of from about 30 to about 100 nanometers. The preferred range being dictated by the optical constants of the anode material.

The hole transport layer is preferably of from about 5 to about 500 nanometers, and more preferably, of from about 10 to about 200 nanometers.

The organic film/layer is preferably of from about 5 to about 500 nanometers, and more preferably, of from about 10 to about 200 nanometers.

The light emitting layer is preferably of from about 5 to about 500 nanometers, and more preferably, of from about 10 to about 200 nanometers.

The electron transport layer is preferably of from about 5 to about 500 nanometers and more preferably, of from about 10 to about 200 nanometers.

The cathode layer is preferably of from about 10 to about 500 nanometers.

In a preferred embodiment, an organic EL device is provided that comprises, in sequence, glass as the supporting substrate; an anode thereover of indium tin oxide in a thickness of from about 1 to about 500 nanometers; in contact with the anode, a hole transport layer of a polymeric tertiary aromatic amine material having a thickness of from about 5 to about 500 nanometers; thereover the hole transport layer, an electron transport layer comprised of a triazine polymer or copolymer described herein, in a thickness of from about 5 to about 500 nanometers; and in contact therewith, a low work function metal as a cathode. In these particular EL devices, light emission originates from the electron transport layer of the triazine polymer or copolymer.

In another preferred embodiment, an organic EL device is provided that comprises, in sequence, glass as the supporting substrate; an anode thereover of indium tin oxide in a thickness of from about 1 to about 500 nanometers; in contact with the anode, a hole transport layer comprised of a polymeric luminescent material, such as poly (phenylvinylene) having a thickness of from about 5 to about 500 nanometers; thereover the hole transport layer, an electron transport layer comprised of a triazine polymer or copolymer described herein, in a thickness of from about 5 to about 500 nanometers; and in contact therewith, a low work function metal as a cathode. In these particular EL devices, light emission originates from the hole transport layer and/or the electron transport layer.

In yet another preferred embodiment, an organic EL device is provided that comprises, in sequence, glass as the supporting substrate; an anode thereover of indium tin oxide in a thickness of from about 1 to about 500 nanometers; in contact with the anode, a hole transport layer of a polymeric tertiary aromatic amine material having a thickness of from about 5 to about 500 nanometers; there over the hole transport layer, a light emitting layer comprised of a polymeric luminescent materials, such as a poly(fluorene), preferably a cured poly(fluorene), having a thickness of from about 5 to about 500 nanometers; thereover the light emitting layer, an electron transport layer comprised of a triazine polymer or copolymer described herein, in a thickness of from about 5 to about 500 nanometers; and in contact therewith, a low work function metal as a cathode.

It is desirable that the organic EL devices of the present invention comprise a support substrate. Illustrative examples of support substrates include polymeric components, glass and the like. For instance, polyesters like MYLAR™, polycarbonates, polyacrylates, polymethacrylates, polysulfones, quartz, and the like. Other substrates can also be selected provided, for example, it can effectively support the other layers, and that it does not interfere with the device functional performance.

Examples of the anode, which is contiguous to the substrate, include positive charge injecting electrodes such as indium tin oxide, tin oxide, gold, platinum, or other suitable materials, such as electrically conductive carbon, conjugated polymers such as polyaniline, polypyrrole, and the like. Preferably, the anode has a work function equal to, or greater than, about 4 electron volts, and more preferably, from about 4 to about 6 electron volts.

The hole transporting layer may be comprised of any suitable hole transporting material. It is desirable that the materials selected possess a resistance to erosion by the coating solutions thereover. Illustrative examples of such polymeric hole transport materials include polycarbazoles, polymeric arylamines, such as those disclosed in U.S. Pat. No. 5,728,801 and herein incorporated by reference, polyaniline and its acid-doped forms, polythiophene and its acid-doped forms, polypyrrole, poly(phenylvinylene), and the like. The hole transporting layer may be prepared using various means well known in the art, including spin-coating, spray-coating, dip-coating, roller-coating, screen-coating and the like.

Examples of light emitting compounds for forming the light emitting layer include any suitable polymeric luminescent material known in the art. Specific examples of such luminescent materials include the triazine polymers or copolymers described herein; poly(phenylvinylenes) (G. Leising et al., Adv. Mater. 4 (1992), No. 1; Friend et al., J. Chem. Soc., Chem. Commun. 1992, p. 32–34; Saito et al., Polymer, 1990, Vol. 31, 1137; Friend et al., Physical Review B, Vol. 42, No. 18, 11670); poly(fluorenes), preferably the curable poly(fluorenes) such as those disclosed in U.S. Pat. No. 5,962,631; and the like. These references are herein incorporated by reference. The polymeric light emitting layer can be prepared by forming one of the polymers into thin films by known methods, such as spin-coating, spray-coating, dip-coating, roller-coating, screen-coating and the like.

Examples of electron transport materials for forming the electron transport layer include any suitable organic electron transport materials known in the art. Specific examples of such electron transport materials include the triazine polymers or copolymers of the present invention and the metal chelates of 8-hydroxyquinoline as disclosed in U.S. Pat. Nos. 4,539,507, 5,151,629, and 5,150,006, herein incorporated by reference. Some examples of the metal chelates of 8-hydroxyquinoline are tris(8-hydroxyquinolinate) aluminum, tris(8-hydroxyquinolinate) gallium, bis(8-hydroxyquinolinate) magnesium, bis(8-hydroxyquinolinate) zinc, tris(5-methyl-8-hydroxyquinolinate) aluminum, tris(7-propyl-8-quinolinolato) aluminum, bis[benzo[f]-8-quinolinate] zinc, bis(10-hydroxybenzo[h]quinolinate) beryllium, and the like. Another class of electron transport materials that may be used are the non-polymeric triazine compounds as disclosed in U.S. Pat. No. 6,225,467, herein incorporated by reference. Some examples of the non-polymeric triazine compounds are 4,4'-bis-[2-(4,6-diphenyl-1,3,5-triazinyl)]-1,1'-biphenyl, 4,4'-bis-[2-(4,6-di-p-tolyl-1,3,5-triazinyl)]-1,1'-biphenyl, 4,4'-bis-[2-(4,6-di-m-tolyl-1,3,5-triazinyl)]-1,1'-biphenyl, 4,4'-bis-[2-(4,6-di-p-methoxyphenyl-1,3,5-triazinyl)]-1,1'-biphenyl, 4,4'-bis-[2-(4,6-di-m-methoxyphenyl-1,3,5-triazinyl)]-1,1'-biphenyl, 4,4'-bis-[2-(4-o-naphthyl-6-phenyl-1,3,5-triazinyl)]-1,1'-biphenyl, 4,4'-bis-[2-(4,6-di-phenyl-1,3,5-triazinyl)]-stilbene, 2,4,6-tris(4-biphenyl)-1,3,5-triazine, and the like.

The cathode may be comprised of any suitable material, such as metals with a high work function component equal to, for example, about 4.0 eV to about 6.0 eV, or a low work function component equal to, for example, about 2.5 eV to about 4.0 eV. The cathode can be derived from a combination of a low work function metal and at least one other metal. Effective proportions of the low work function metal to the at least one other metal are from less than about 0.1 percent to about 99.9 percent by weight. Illustrative examples of low work function metals include alkaline metals, such as lithium or sodium; Group 2A or alkaline earth metals, such as beryllium, magnesium, calcium, or barium; and Group III metals including rare earth metals and the actinide group metals, such as scandium, yttrium, lanthanum, cerium, europium, terbium, or actinium. Lithium, magnesium and calcium are preferred low work function metals. The magnesium/silver cathodes of U.S. Pat. No. 4,885,211 constitute a preferred cathode construction and is herein incorporated by reference. Another preferred cathode is described in U.S. Pat. No. 5,429,884, herein incorporated by reference, and includes cathodes formed from lithium alloys with other high work function metals such as aluminum and indium.

Both the anode and the cathode of the EL devices of the present invention may contain a protective coating thereon, and the anode and cathode may be of any convenient form. A thin conductive anode or cathode layer may be coated onto a light transmissive substrate, for example, a transparent or substantially transparent glass plate or plastic film. For instance, the EL device can include a light transmissive anode formed from tin oxide or indium tin oxide coated on a glass plate. This coating can be very thin, for example, less than about 200 Å, and more specifically, from about 75 Å to about 150 Å. Light-transparent metallic anodes can be used, such as gold, palladium, and the like. In addition, transparent or semi-transparent thin layers, for example from 50 Å to about 175 Å, of conductive carbon or conjugated polymers, such as polyaniline, polypyrrole, and the like, may be selected as anodes. Additional suitable forms of the anode and cathode are illustrated in U.S. Pat. No. 4,885,211, herein incorporated by reference.

EXAMPLES

The following examples are being submitted to further illustrate various embodiments of the present invention. These examples are intended to be illustrative only and are not intended to limit the scope of the present invention.

Example I

Synthesis of 2,6-bis(4-bromophenyl)-4-phenyl-1,3,5-triazine:

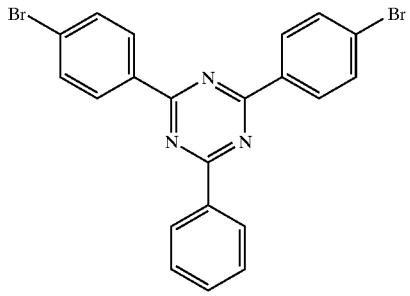

In a 100 milliliter round bottom flask there was added benzoyl chloride (2.8 grams), 1,2-dichlorobenzene (50 milliliters), thionyl chloride (0.5 milliliters), and aluminum chloride (2.7 grams) with stirring, and p-bromobenzonitrile (7.6 grams) was added slowly. The resulting reaction mixture was heated under argon to about 150° C. for 0.5 hours. The temperature of the reaction mixture was reduced to 120° C. and then ammonium chloride (2.14 grams) was added. The resulting reaction mixture was stirred at 150° C. for an additional 20 hours. The reaction flask was cooled to room temperature (about 25° C.). The resulting mixture was poured into 600 milliliters of methanol and stirred for 20 minutes. The resulting precipitate was collected by filtration and dried in a vacuum oven to afford 5.5 grams of crude product, which was further purified by sublimation.

Example II

Synthesis of 2-(1,1'-biphenyl-4-yl)-4,6-bis(4-bromophenyl)-1,3,5-triazine:

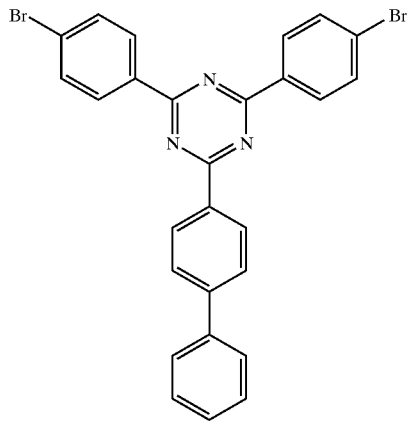

In a 250 milliliter round bottom flask there was added 4-biphenylcarbonyl chloride (4.3 grams), 1,2-dichlorobenzene (50 milliliters), thionyl chloride (0.5 milliliter), and aluminum chloride (2.6 grams) with stirring, and p-bromobenzonitrile (7.6 grams) was added slowly. The resulting reaction mixture was heated under argon to about 150° C. for 0.5 hours. The temperature of the reaction mixture was reduced to 120° C., and then ammonium chloride (2.14 grams) was added. The reaction mixture was stirred at this temperature for an additional 20 hours. The reaction flask was cooled to room temperature (about 25° C.). The resulting mixture was poured into 600 milliliters of methanol and stirred for 20 minutes. The resulting precipitate was collected by filtration and dried in a vacuum oven to afford 7.6 grams of crude product, which was further purified by sublimation.

Example III

Synthesis of 2,7-dibromo-9,9-di-n-hexylfluorene:

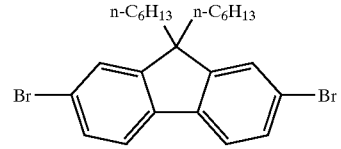

In a 250 milliliter round bottom flask there was added 2,7-dibromofluorene (6.45 grams), n-hexyl bromide (16.5 grams), tetra-n-butylammonium chloride (0.5 grams), and a 50 weight % aqueous sodium hydroxide solution. The resulting mixture was stirred at 80° C. for 3 hours. After cooling to ambient temperature, about 23° C., the product mixture was transferred to a separatory funnel and extracted with toluene. The toluene extracts were washed with water and dried over anhydrous magnesium sulfate. Removal of the organic solvent by evaporation afforded an oily residue, which was crystallized from ethanol to provide 8.8 grams of 2,7-dibromo-9,9-di-n-hexylfluorene as colorless crystals.

Example IV

Synthesis of 2,7-dibromo-9,9-di-n-octylfluorene:

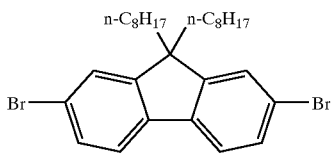

This compound was prepared from 2,7-dibromofluorene and n-octyl bromide, using a similar procedure as described in Example III. The product was obtained in an 85% yield as colorless crystals.

Example V

Synthesis of 9,9-di-n-hexyl-2,7-bis(4,4,5,5-tetramethyl-1,2,3-dioxaborolan-2-yl)fluorene:

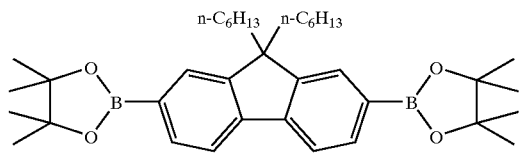

In a 250 milliliter round bottom flask, 2,7-dibromo-9,9-di-n-hexylfluorene (4.92 grams) and anhydrous diethyl ether (50 ml) was added and kept under an argon atmosphere. The reaction mixture was cooled to around 0° C. and 25 milliliters of tert-butyl lithium (1.7 M pentane solution) was added over about 15 minutes. The reaction mixture was stirred for 30 minutes and then allowed to warm to ambient temperature, about 23° C., for an additional 10 minutes. After re-cooling the mixture to −78° C. using a dry ice/acetone bath, 2-isopropoxy-4,4,5,5-tetramethyl-1,2,3-dioxaborolane (4.5 g) was added, the cooling bath was removed, and the reaction mixture was stirred for about 6 hours. The mixture was diluted with toluene, washed with a brine solution, and dried over anhydrous magnesium sulfate. Removal of the organic solvent by evaporation afforded an oily residue, which was crystallized from hexane to provide 4.5 grams of 9,9-di-n-hexyl-2,7-bis(4,4,5,5-tetramethyl-1,2,3-dioxaborolan-2-yl)fluorene as colorless crystals.

Example VI

Synthesis of 9,9-di-n-octyl-2,7-bis(4,4,5,5-tetramethyl-1,2,3-dioxaborolan-2-yl)fluorene:

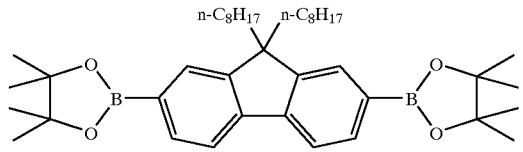

This compound was prepared from 2,7-dibromo-9,9-di-n-hexylfluorene, using a similar procedure as described in Example V. The product was obtained in a 75% yield as colorless crystals.

Example VII

Synthesis of Triazine Copolymer:

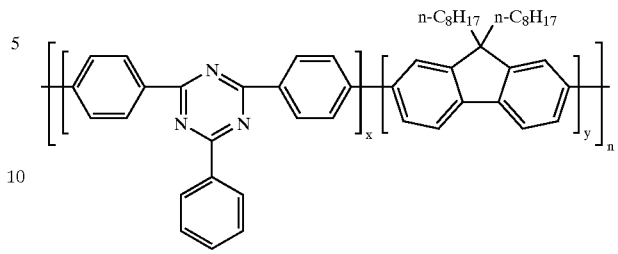

$x=0.1$, $y=0.9$

In a 200 ml round-bottom flask was added 2,6-bis(4-bromophenyl)-4-phenyl-1,3,5-triazine (0.467 grams, 1.0 mmol), 9-di-n-octyl-2,7-dibromofluorene (2.468 grams, 4.5 mmol), 9,9-di-n-octyl-2,7-bis(4,4,5,5-tetramethyl-1,2,3-dioxaborolan-2-yl)fluorene (2.892 g, 4.5 mmol), Aliquat-336™ (1.0 g, a phase transfer catalyst purchased from Aldrich Chemicals, Milwaukee, Wis., USA), a 2M aqueous sodium carbonate solution (10 milliliters), and toluene (50 milliliters). The resulting mixture was stirred under argon for 10 min, followed by the addition of tetrakis (triphenylphosphine) palladium (52 mg). The reaction mixture was heated to gentle reflux and stirred for 20 hours. Bromobenzene (1.0 ml) was added to the mixture, and the resulting mixtures was stirred and refluxed for an additional 1 hour. The mixture was cooled to room temperature (about 25° C.), diluted with toluene (~100 milliliters). The organic layer was separated, washed successively with deionized water, 10% HCl, and deionized water, and then dried over anhydrous magnesium sulfate. Filtration through celite to resulted in a toluene solution containing the copolymer product, which was precipitated from methanol to provide the triazine copolymer as a whitish powder. The $M_w$ (weight average molecular weight) is 84,700.

Example VIII

Synthesis of Triazine Copolymer:

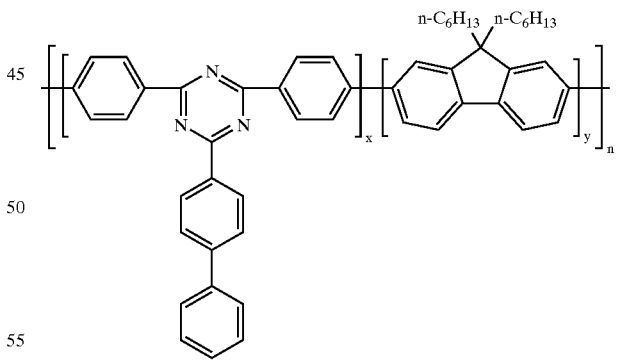

$x=0.1$, $y=0.9$

This copolymer was prepared from 2-(1,1'-biphenyl-4-yl)-4,6-bis(4-bromophenyl)-1,3,5-triazine, using a similar procedure as described in Example VII. The product was obtained as a whitish powder.

Other modifications of the present invention will or may occur to those of ordinary skill in the art subsequent to a review of the present application. These modifications and equivalents thereof are intended to be included within the scope of the present invention.

What is claimed is:

1. A triazine compound of Formula I:

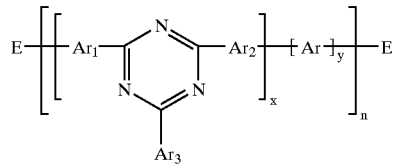

(I) a triazine compound of Formula II:

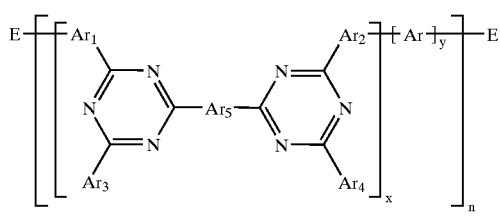

(II) a triazine compound of Formula III:

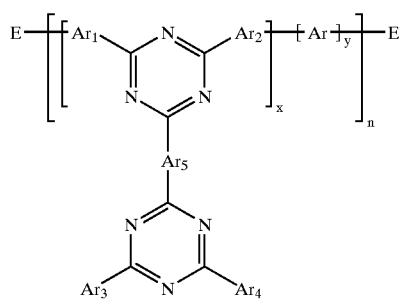

(III) wherein E is an end-capping group; Ar, $Ar_1$, $Ar_2$, $Ar_3$, $Ar_4$ and $Ar_5$ are each independently selected from the group consisting of an aromatic group and a heteroaromatic group containing nitrogen, oxygen or sulfur; x and y each represent molar fractions of corresponding monomers, wherein the total molar fraction of x and y is 1; and n represents a number of repeating units; and wherein the compounds of Formulas I, II and ill each independently represent at least one of an alternating copolymer, a random copolymer, a block copolymer and a graft copolymer.

2. A triazine compound of Formula IV:

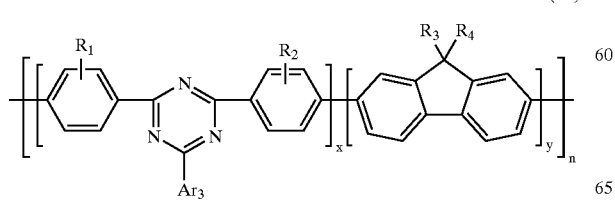

a triazine compound of Formula V:

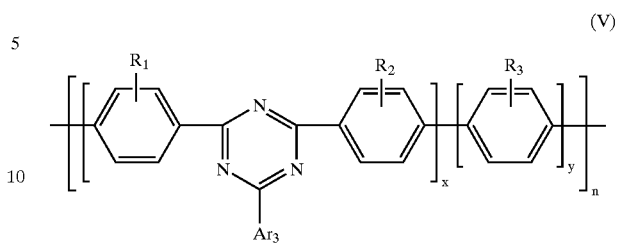

a triazine compound of Formula VI:

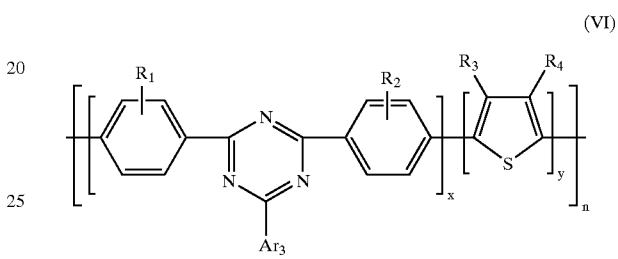

wherein $R_1$ and $R_2$ are each independently selected from the group consisting of a hydrogen, a halide, an alkyl group containing from about 1 to 20 carbons, an aromatic group, a heteroaromatic group containing nitrogen, oxygen or sulfur, an alkoxy group containing from about 1 to 20 carbons, a phenoxy group, and a cyano group; $R_3$ and $R_4$ are each independently Selected from the group consisting of a hydrogen; a fluorine; an alkyl group containing from about 1 to 20 carbons; an alkyl group containing from about 1 to 20 carbons and at least one heteroatom selected from the group consisting of oxygen, sulfur, and silicon; an aromatic group; a heteroaromatic group containing nitrogen, oxygen or sulfur; an alkoxy group containing from about 1 to 20 carbons; a phenoxy group; and a cyano group; $Ar_3$ is selected from the group consisting of an aromatic group and a heteroaromatic group containing nitrogen, oxygen or sulfur; x and y each represent molar fractions of corresponding monomers, wherein the total molar fraction of x and y is 1; and n represents a number of repeating units; and wherein the compounds of Formulas IV, V and VI each independently represent at least one of an alternating copolymer, a random copolymer, a block copolymer and a graft copolymer.

3. A triazine compound of the Formula I:

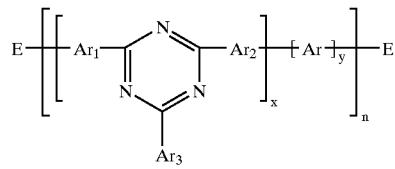

wherein $Ar_1$ is phenyl, $Ar_2$ is biphenyl, $Ar_3$ is a biphenyl group; Ar is of the formula:

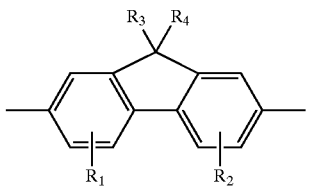

and wherein $R_1$ and $R_2$ are each independently selected from the group consisting of hydrogen, a halide, an alkyl group containing from about 1 to 20 carbons, an aromatic group, a heteroaromatic group containing nitrogen, oxygen or sulfur, an alkoxy group containing from about 1 to 20 carbons, a phenoxy group, and a cyano group; $R_3$ and $R_4$ are each independently selected from the group consisting of a hydrogen; a fluorine; an alkyl group containing from about 1 to 20 carbons; an alkyl group containing from about 1 to 20 carbons and at least one heteroatom selected from the group consisting of oxygen, sulfur, and silicon; an aromatic group; a heteroaromatic group containing nitrogen, oxygen or sulfur; an alkoxy group containing from about 1 to 20 carbons; a phenoxy group; and a cyano group; and E is hydrogen; x and y each represent molar fractions of corresponding monomers, wherein the total molar fraction of x and y is 1; and n represents the number of repeating units.

4. A triazine compound of the formula:

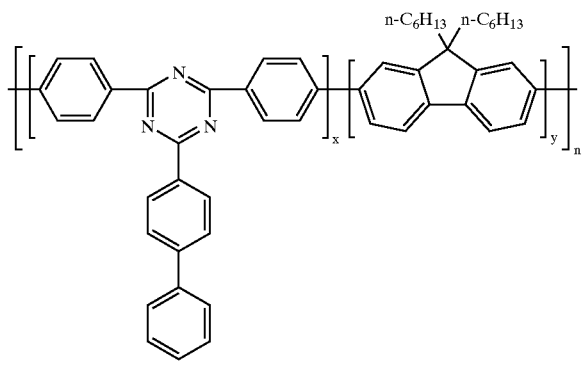

wherein x is equal to 0.1 and y is equal to 0.9, and wherein n represents the number of repeating units.

5. A triazine compound according to claim 1 wherein x is about 0.01 to 1, y is less than about 0.99, and n is a number of from about 3 to about 500.

6. A triazine compound according to claim 5, wherein x is about 0.05 and y is about 0.95.

7. A triazine compound according to claim 1 wherein the $M_w$ (weight average molecular weight) of the triazine compound is from about 1,000 to 100,000.

8. A triazine compound according to claim 2 wherein x is about 0.01 to 1, y is less than about 0.99, and n is a number of from about 3 to about 500.

9. A triazine compound according to claim 8, wherein x is about 0.05 and y is about 0.95.

10. An electroluminescent device comprising an anode, a cathode, and an organic film/layer between the anode and cathode, wherein said organic film/layer is comprised of a triazine compound according to claim 1.

11. An electroluminescent device comprising an anode, a cathode, and an organic film/layer between the anode and cathode, wherein said organic film/layer is comprised of a triazine compound according to claim 2.

12. An electroluminescent device comprising, in sequence, an anode, a hole transport layer, an electron transport layer and a cathode, wherein said electron transport layer is comprised of a triazine compound according to claim 1.

13. An electroluminescent device comprising, in sequence, an anode, a hole transport layer, an electron transport layer and a cathode, wherein said electron transport layer is comprised of a triazine compound according to claim 2.

14. An electroluminescent device according to claim 12 wherein said hole transport layer is selected from a group consisting of polyaniline and its acid-doped forms, polythiophene and its acid-doped forms, polycarbazoles, and polymeric arylamines.

15. An electroluminescent device according to claim 12, wherein at least one of said electron transport layer and said hole transport layer is a light emitting layer.

16. An electroluminescent device comprising, in sequence, an anode, a hole transport layer, a light emitting layer, an electron transport layer and a cathode, wherein one of said light emitting layer and said electron transport layer is comprised of a triazine compound according to claim 1.

17. An electroluminescent device comprising, in sequence, an anode, a hole transport layer, a light emitting layer, an electron transport layer and a cathode, wherein one of said light emitting layer and said electron transport layer is comprised of a triazine compound according to claim 2.

* * * * *